US00PP14478P29

(12) United States Plant Patent
Slaughter et al.

(10) Patent No.: US PP14,478 P2
(45) Date of Patent: Jan. 20, 2004

(54) PEACH TREE NAMED 'BURPEACHSEVENTEEN'

(50) Latin Name: *Prunus persica*
Varietal Denomination: Burpeachseventeen

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/353,251

(22) Filed: Jan. 27, 2003

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of peach tree (*Prunus persica*), and which is denominated varietally as 'Burpeachseventeen', and which produces an attractively colored yellow-fleshed, clingstone peach which is mature for harvesting approximately July 17 to July 25 under ecological conditions prevailing in the San Joaquin Valley of Central California.

1 Drawing Sheet

BACKGROUND OF THE NEW VARIETY

The present invention relates to a new, novel and distinct variety of peach tree, *Prunus persica*, which has been denominated varietally as 'Burpeachseventeen'.

ORIGIN

The present variety of peach tree resulted from an on-going program of fruit and nut tree breeding. The purpose of this program is to improve the commercial quality of deciduous fruit and nut varieties, and rootstocks, by creating and releasing promising new selections of prunus, malus and regia species. To this end we make both controlled and hybrid cross pollinations each year in order to produce seedling populations from which improved progenies are evaluated and selected.

The seedling 'Burpeachseventeen' was originated by us from a population of seedlings grown in our experimental orchards located near Fowler, Calif. The seedlings, grown on their own roots, were the result of a controlled cross of the yellow-fleshed, clingstone peach tree, 'Ross', (U.S. Plant Pat. No. 4,863), which was used as the seed parent, and the yellow-fleshed, clingstone peach tree, 'H6-55', (unpatented), which was used as the pollen parent. One seedling, which is the present variety, exhibited especially desirable characteristics and was designated as 'C17.044'. This seedling was marked for subsequent observation. After the 1997 fruiting season, the new variety of peach tree was selected for advanced evaluation and repropagation.

ASEXUAL REPRODUCTION

Asexual reproduction of this new and distinct variety of peach tree was accomplished by budding the new peach tree to 'Nemaguard' Rootstock (non-patented). This was performed by us in our experimental orchard which is located near Fowler, Calif. Subsequent evaluations have shown those asexual reproductions run true to the original tree. All characteristics of the original tree, and its fruit, were established and appear to be transmitted through succeeding asexual propagations.

SUMMARY OF THE VARIETY

'Burpeachseventeen' is a new and distinct variety of peach tree, which is considered of large size, and which has vigorous growth. This new peach tree is also a regular and productive bearer of relatively large, firm, yellow fleshed, clingstone fruit, which have good flavor and eating qualities. This new tree displays a chilling requirement of approximately 650 hours, and further produces relatively uniformly sized fruit throughout the entire tree. The fruit produced by this new variety of peach tree has a non-melting flesh which makes it ideal for canning. In addition to the foregoing the fruit of this new tree also appears to have good handling and shipping qualities. The 'Burpeachseventeen' peach tree bears fruit which are ripe for commercial harvesting and shipment on approximately July 17 to July 25 under the ecological conditions prevailing in the San Joaquin Valley of central California. In relative comparison with the 'Ross' peach tree, which is the seed parent, the present new variety of peach tree bears fruit which ripen about 8 days earlier at the same geographical location.

BRIEF DESCRIPTION OF THE DRAWING

The accompanying drawing, which is provided, is a color photograph of the new variety of peach tree. The photograph depicts two whole mature fruit, and one mature fruit dissected substantially in the equatorial plane, and which reveals the flesh and the stone characteristics thereof. The external coloration of the fruit as shown is sufficiently matured for harvesting and shipment. Additionally the photograph displays a sample vegetative shoot bearing typical leaves, and a typical stone, with the flesh removed. The colors in this photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society) and descriptions provided hereinafter.

DETAILED DESCRIPTION

Referring more specifically to the pomological details of this new and distinct variety of peach tree, the following was observed during the fifth fruiting season under the ecological conditions prevailing at orchards located near the town of Fowler, county of Fresno, state of California. All major color code designations are by reference to The R.H.S. Colour Chart (Fourth Edition) provided by The Royal Horticultural Society of Great Britain. Common color names are also occasionally used.

Tree:

*Size.*—Generally — Considered medium-large as compared to other common commercial peach cultivars ripening in the early season of maturity. The trees of the present variety were pruned to a height of approximately 301.0 cm to about 320.0 cm at maturity.

*Vigor.*—Considered moderately vigorous. The present peach tree variety grew from about 144.0 cm to 152.0 cm in height during the first growing season. The new variety was pruned to a height of approximately 130.0 cm in the first dormant season, and primary scaffolds were then selected for the desired tree structure.

*Productivity.*—Productive. Fruit set varies from twice to several times more than the desired crop load. The fruit set is spaced by thinning to develop the remaining fruit into the desired market size. The number of the fruit set varies with the prevailing climatic conditions, and cultural practices employed during the bloom period and is therefore not distinctive of this variety.

*Bearer.*—Regular. Fruit set has been heavy during the years of observation and thinning was necessary during the past 5 years.

*Form.*—Upright, and pruned to a vase shape.

*Density.*—Considered medium dense. It has been discovered that pruning the branches from the center of the tree to obtain a resulting vase shape allows for air movement and appropriate amounts of sunlight to enhance fruit color and renewal of fruiting wood throughout the tree.

*Hardiness.*—The present tree was grown and evaluated in USDA Hardiness Zone 9. Winter chilling requirements of the new tree are approximately 650 hours below 7.0 degrees C. The variety also appears to be hardy under typical Central San Joaquin Valley conditions.

Trunk:

*Diameter.*—Approximately 15.0 cm in diameter when measured at a distance of approximately 15.24 cm above the soil level. The measurement was taken at the end of the fifth growing season.

*Bark texture.*—Considered moderately rough, with numerous folds of papery scarfskin being present.

*Lenticels.*—Numerous flat, oval lenticels are present. The lenticels range in size from approximately 4.0 to about 6.0 millimeters in width, and from 1.0 to about 2.0 millimeters in height.

*Lenticel color.*—Considered an orange brown, (RHS Greyed Orange Group N172 A).

*Bark coloration.*—Variable, but it is generally considered to be a gray brown, (RHS Brown Group 200 D).

Branches:

*Size.*—Considered average for the variety.

*Diameter.*—Average as compared to other peach varieties. The branches have a diameter of about 7.5 centimeters when measured during the fifth year following grafting.

*Surface texture.*—Average, and appearing furrowed on wood which is several years old.

*Crotch angles.*—Primary branches are considered variable between about 47 to 53 degrees when measured from the horizontal axis. This particular characteristic is not considered distinctive of the variety however.

*Current season shoots.*—Surface texture — Substantially glabrous.

*Internode length.*—Approximately 2.5 to about 2.7 cm.

*Color of mature branches.*—Medium brown, (RHS Greyed Orange 177 C).

*Current seasons shoots.*—Color — Light green, (RHS Yellow Green Group 146 C). The color of new shoot tips is considered a bright and shiny green (RHS Yellow Green Group 143 C).

Leaves:

*Size.*—Considered medium-large for the species. Leaf measurements have been secured from vigorous, upright, current-season growth taken at approximately mid-shoot.

*Leaf length.*—Approximately 142.0 to about 158.0 millimeters.

*Leaf width.*—Approximately 34.0 to about 39.0 millimeters.

*Leaf base shape.*—Slightly oblique relative to the leaf longitudinal axis.

*Leaf form.*—Lancelolate.

*Leaf tip form.*—Acuminate.

*Leaf color.*—Upper leaf surface — Dark green, (approximately RHS Green Group 141 B).

*Leaf texture.*—Glabrous.

*Leaf color.*—Lower Leaf Surface — Medium green, (RHS Green Group 146 B).

*Leaf venation.*—Pinnately veined.

*Mid-vein.*—Color — Light yellow green, (RHS Yellow Green Group 145 C).

*Leaf margins.*—Slightly undulating. Form — Considerably serrate. Uniformity — Considered generally uniform.

*Leaf petioles.*—Size — Considered average. Length — About 7.0 to about 10.5 mm. Diameter — About 1.5 to about 2.0 mm. Color — Pale green, (RHS Yellow Green Group N144 D).

*Leaf glands.*—None can be readily detected with the unaided eye.

*Leaf stipules.*—Size — Medium large for the variety. Number — Typically 2 per leaf bud and up to 6 per shoot tip. Form — Lanceolate in form and having a serrated margin. Color — Green, (RHS Yellow Green Group 144 A) when young, but graduating to a brown color, (RHS Grey Orange group 166 B) with advancing senescence. The stipules are considered to be early deciduous.

Flowers:

*Flower buds.*—Generally — The floral buds, depending upon the stage of development, are approximately 6.0 millimeters wide; about 10.0 millimeters long; conic in form; and slightly appressed relative to the bearing shoot.

*Flower buds.*—Color — This characteristic is dependent upon the proximity to the bloom. The bud scales are reddish-purple, (approximately RHS Greyed Purple Group 187 A). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress and therefore this information is not available.

*Date of first bloom.*—Mar. 3, 2002.

*Blooming time.*—Considered mid-season in relative comparison to other commercial peach cultivars grown in the central San Joaquin Valley. The date of full bloom was observed on Mar. 8, 2002. The date of bloom varies slightly with the prevailing climatic conditions and cultural practices.

*Duration of bloom.*—Approximately 9 days. This characteristic varies slightly with the prevailing climatic conditions.

*Flower type.*—The variety is considered to have a showy type flower.

*Flower size.*—The flower diameter at full bloom is approximately 43.0 to about 46.0 millimeters.

*Bloom quantity.*—Considered abundant.

*Flower bud frequency.*—Normally 1 to 2 flower buds appear per node.

*Petal size.*—Generally — Considered large for the species. Length — Approximately 18.0 to about 20.0 millimeters. Width — Approximately 19.0 to about 22.0 millimeters.

*Petal form.*—Slightly truncate.

*Petal count.*—Nearly always 5.

*Petal texture.*—Glabrous.

*Petal color.*—Light pink, (RHS Red Purple Group 65 C), and darkening to a medium pink, (RHS Red Purple Group 68 C).

*Fragrance.*—Slight.

*Petal claw.*—Form — The claw is considered truncate in shape and has a large size when compared to other varieties. Length — Approximately 9.0 to about 11.0 millimeters. Width — Approximately 10.0 to about 13.0 millimeters.

*Petal margins.*—Generally considered variable, from nearly smooth to slightly ruffled, to moderately undulate.

*Petal apex.*—Generally — The petal apices generally appear slightly grooved at the tip.

*Flower pedicel.*—Length — Considered medium-long, and having an average length of approximately 3.0 to about 4.0 millimeters. Diameter — Considered average, approximately 2.0 millimeters. Color — A medium brown, (RHS Greyed Orange Group N167 D).

*Floral nectaries.*—Color — A Dull orange, (RHS Greyed Orange Group 169 A).

*Calyx.*—Surface Texture — Generally glabrous. Color — A dull reddish purple, (approximately RHS Greyed Purple Group 183 B).

*Sepals.*—Surface Texture — The surface has a short, fine pubescent texture. Size — Average, and ovate in form. Color — A dull red, (approximately RHS Greyed-Purple Group 187 A).

*Anthers.*—Generally — Average to above average in length. Color — A dark reddish-purple dorsally, (approximately RHS Greyed Purple Group 187 A).

*Pollen production.*—Pollen is abundant, and has a yellow color, (approximately RHS Yellow Orange Group 17 B).

*Filaments.*—Size — Length is variable, approximately 13.0 to 16.0 millimeters long. Color — Considered light pink, (RHS Red Group 56 D).

*Pistil.*—Number — Usually 1, rarely 2. Size — Average. Length — Approximately 16.0 to about 19.0 millimeters including the ovary. Color — Considered a very pale green, (approximately RHS Yellow Green Group 150 C). Surface Texture — The variety has a long pubescent pistil.

Fruit:

*Maturity when described.*—Firm ripe condition (shipping ripe). Date of first picking — Jul. 17, 2002. Date of last picking — Jul. 27, 2002. The date of harvest varies slightly with prevailing climatic conditions.

*Size.*—Generally — Considered large, and uniform.

*Average cheek diameter.*—Approximately 69.0 to about 72.0 millimeters.

*Average axial diameter.*—Approximately 67.0 to about 68.0 millimeters.

*Typical weight.*—Approximately 287.0 grams. This characteristic is highly dependent upon the prevailing cultural practices, and therefore is not particularly distinctive of the variety.

*Fruit form.*—Generally — Moderately oblate. When viewed from the axial plane the fruit will appear to have a slightly extended suture plane. The fruit is generally uniform in symmetry.

*Fruit suture.*—Shallow and extending from the base to apex. No apparent callousing or stitching exists along the suture line.

*Suture.*—Color — This has a yellow background color, (approximately RHS Yellow Orange Group 17 A).

*Ventral surface.*—Form — Slightly indented.

*Apex.*—Rounded.

*Base.*—Generally retuse.

*Stem cavity.*—Generally elongated in the suture plane. Average depth of the stem cavity is about 1.0 cm. Average width of the stem cavity is about 1.2 cm.

*Fruit skin.*—Thickness — Considered medium in thickness, and tenacious to the flesh. Texture — Short, fine, and pubescent. The pubescence is reasonably abundant. Taste — Non-astringent. Tendency to crack — None observed.

*Color.*—Blush Color — This blush color appears as a faint red flecking on a minority of the skin of the fruit (approximately RHS Red Group 45 A), and generally is more present on the basal portions of the fruit. Ground Color — Yellow-orange, (approximately RHS Yellow Orange Group 17 A).

*Fruit stem.*—Medium in length, approximately 5.0 to about 7.0 millimeters. Diameter — Approximately 2.0 to about 3.0 millimeters. Color — Pale yellow-green, (approximately RHS Yellow Green Group 145 B).

*Flesh.*—Ripens — Evenly. Texture — Firm, and dense. Considered non-melting. Fibers — Few, small, and tender ones are found. Aroma — Very slight. Eating Quality — Considered very good. Flavor — Considered sweet and mildly acidic. The flavor is viewed as both pleasant and balanced. Juice Production — Moderate. Brix — About 12.5 degrees. This characteristic varies slightly with the number of fruit per tree; prevailing cultural practices; and the surrounding climatic conditions. Flesh Color — Pale yellow, (approximately RHS Yellow Orange Group 20 A).

Stone:

*Type.*—Clingstone.

*Size.*—Considered medium large for the variety. The stone size varies significantly depending upon the tree vigor, crop load and growing conditions.

*Length.*—Average, about 25.0 to about 30.0 millimeters.

*Width.*—Average, about 22.0 to about 25.0 millimeters.

*Diameter.*—Average, about 16.0 to about 18.0 millimeters.

*Form.*—Obovoid.

*Base.*—The stone is usually rounded to slightly oblique relative to the ventral side.

*Apex.*—Shape — The stone apex is raised and reasonably prominent and having a sharp, acute tip.

*Stone surface.*—Surface Texture — Irregularly furrowed toward the basal end. Pitting is considered abundant, but is as a general matter more typically noted on the lateral sides. Ridges — The surface texture is generally characterized by less prominent ridges, and narrow and more shallow inter-ridge troughs. Ventral Edge — Width — Considered average, and having a dimension of approximately 2.0 to 4.0 millimeters when measured at about the mid-suture. Dorsal Edge — Shape — Full, lightly grooved, and having a reasonably smooth margin.

*Stone color.*—The color of the dry stone is generally considered a reddish brown. (approximately Greyed Red Group RHS 178 A).

*Tendency to split.*—Observed, but this is rare.

*Kernel.*—Size — The kernel is considered medium-large. Form — Considered ovoid. Pellicle — Pubescence. Color — (RHS Greyed Orange Group 164 A).

*Use.*—The subject variety 'Burpeachseventeen' is considered to be a Peach tree of the early-mid season maturity, and which produces fruit which are considered firm, attractively colored, and which are useful for both local and long distance shipping.

*Keeping quality.*—Excellent. Fruit has stored well up to 25 days after harvest at 1.0 degree Celsius.

*Shipping quality.*—Good. The fruit of the new peach tree variety showed minimal bruising of flesh or skin damage after being subjected to normal harvesting and packing procedures.

*Resistance to insects and disease.*—No particular susceptibilities were noted. The present variety has not been tested to expose or detect any susceptibilities or resistances to any known plant and/or fruit diseases.

Although the new variety of peach tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety of peach tree, what we claim is new and desire to secure by Plant Letters Patent is:

1. A new distinct variety of peach tree, substantially as illustrated and described, and which is characterized principally as to novelty by producing an attractively colored yellow-fleshed, clingstone peach which is mature for harvesting approximately July 17 to July 25 under the ecological conditions prevailing in the San Joaquin Valley of Central California.

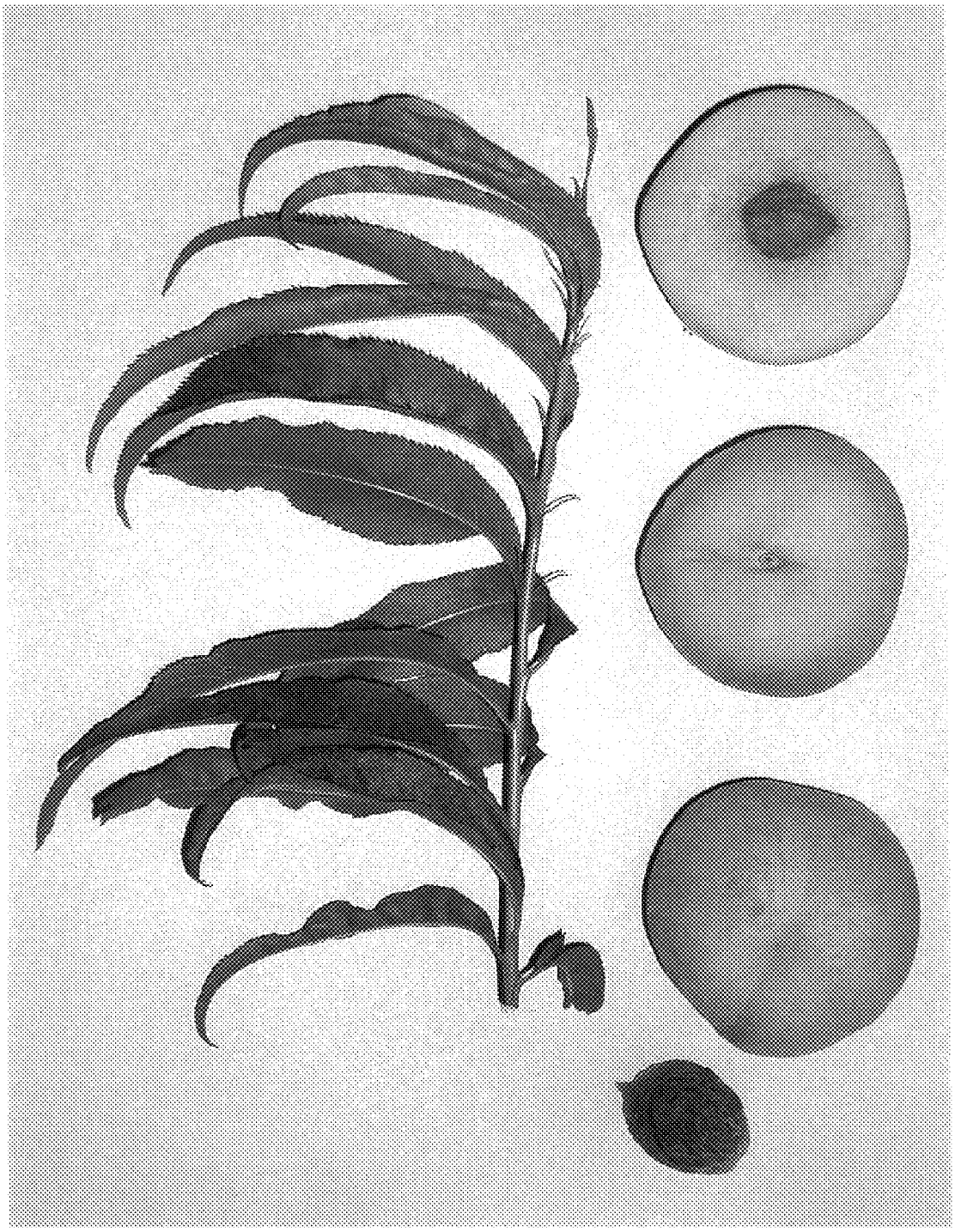

* * * * *